US00PP37586P2

(12) United States Plant Patent
Olesen

(10) Patent No.: US PP37,586 P2
(45) Date of Patent: Aug. 18, 2026

(54) MINIATURE ROSE PLANT NAMED 'POULPAL106'

(50) Latin Name: *Rosa hybrida*
Varietal Denomination: Poulpal106

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/831,802

(22) Filed: Sep. 15, 2025

(30) Foreign Application Priority Data

Sep. 19, 2024 (QZ) ..... PBR 20242188

(51) Int. Cl.
*A01H 5/02* (2018.01)
*A01H 6/74* (2018.01)

(52) U.S. Cl.
USPC ..... Plt./122
CPC ..... *A01H 6/749* (2018.05); *A01H 5/02* (2013.01)

(58) Field of Classification Search
USPC ..... Plt./122, 129, 150
CPC . A01H 5/02; A01H 5/00; A01H 6/749; A01H 6/74
See application file for complete search history.

(56) References Cited

U.S. PATENT DOCUMENTS

PP28,168 P3 * 7/2017 Olesen ..... Plt./150

OTHER PUBLICATIONS

CPVO Community Plant Variety Office Version 4.24.1, retrieved on Dec. 2, 2025 at https://online.plantvarieties.eu/public-ConsultationDetails?registerId=20242188&denomination=poulpal106. 2 pp. (Year: 2025).*

* cited by examiner

*Primary Examiner* — June Hwu

(57) ABSTRACT

A new garden rose plant of the Miniature class which has abundant, orange-red flowers and dark green foliage. This new and distinct variety has shown to be uniform and stable in the resulting generations from asexual propagation.

1 Drawing Sheet

Botanical designation: *Rosa hybrida.*

Variety denomination: 'Poulpal106'.

This application claims priority to Plant Breeder's Rights Application Number 2024/2188, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Odense, Denmark. The new variety, named 'Poulpal106', originated as a single seedling from the stated cross.

The new variety may be distinguished from its male pollen parent and female seed parent primarily by the following characteristics. The male pollen parent plant exhibits flowers with a general tonality of Red Group 40A. The new variety has a distinctly different flower colour of Red Group 43C. The male pollen parent plant grows to a mature height of 80 cm, while the new variety is very compact, growing only 30 cm in height. The female seed parent plant has Red Group 46B flowers with intonations of Red-Purple 61A, while the new variety has Red Group 43C flowers.

The objective of the hybridization of this rose variety was to create a new and distinct variety with unique qualities, such as:

1. Uniform and abundant orange-red flowers;
2. Compact growth when propagated on its own roots;
3. Suitability for production in small containers; and
4. Exceptional disease resistance.

This combination of qualities is not present in previously available commercial cultivars of this type, known to the inventor, and distinguish 'Poulpal106' from all other varieties of which we are aware.

As part of the rose development program, Mogens N. Olesen germinated the seeds from the aforementioned hybridization during winter of 2015 and conducted evaluations on the resulting seedlings in a controlled environment in Odense, Denmark. 'Poulpal106' was selected in the spring of 2016 by the inventor as a single plant from the progeny of the aforementioned hybridization.

Asexual reproduction of 'Poulpal106' by rooted cuttings was first done by Mogens N. Olesen in the nursery in Odense, Denmark in July 2016. This initial and other subsequent asexual propagations conducted in controlled environments have demonstrated that the characteristics of 'Poulpal106' are true to type and are transmitted from one generation to the next.

DESCRIPTION OF THE DRAWING

The accompanying color illustration shows, as true as is reasonably possible to obtain in color photographs of this type, the typical characteristics of the buds, flowers, leaves, and stems, of 'Poulpal106'.

Specifically illustrated in the drawing are open flowers at various stages of development, a cluster of open flowers, demonstrating the abundance of flowers on a branch, sepals and flower petals detached revealing reproductive flower parts, an un-opened flower bud, bare stem exhibiting prickles, mature leaves viewed from above and underneath, and a juvenile leaf exhibiting anthocyanin.

Plants shown are 3 months old.

DETAILED DESCRIPTION OF THE VARIETY

The following is a description of 'Poulpal106', as observed in its growth in a glasshouse nursery in Odense Denmark. Observed plants are 3 months of age, and were grown on their own roots in 17 cm pots. Color references are made using The Royal Horticultural Society (London, England) Colour Chart, 2001, except where common terms of color are used.

For a comparison, several physical characteristics of the rose variety 'Poulpal062', U.S. Plant Pat. No. 28,168, are compared to the claimed plant. While 'Poulpal106' has 137 flower petals, 'Poulpal062' has 50 flower petals. The claimed plant has a flower diameter of 60 mm while 'Poulpal062' has a flower diameter of 75 mm. Open flowers of 'Poulpal106' are generally Red Group 43C in colour, becoming Red Group 52C as the flower matures. The comparison variety, 'Poulpal062', has a general tonality of Red Group 40C becoming Red Group 43C as flowers mature.

Flower and Flower Bud

Blooming habit: Continuous.

Flower bud:

- *Size.*—Upon opening, 18 mm in length from base. of receptacle to end of bud. Bud diameter is 10 mm.
- *Bud form.*—Urceolate.
- *Bud color.*—As sepals divide petals are Red Group 43B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have moderate very weak or no appendages on three of the five sepals.
- *Sepal size.*—About 32 mm long, 8 mm wide.
- *Receptacle.*—Texture: Smooth. Size: 7 mm in height, 11 mm wide. Color: Yellow-Green Group 144A. Shape: Funnel.
- *Pedicel.*—Surface: Smooth. Length: About 35 mm. Diameter: 3 mm on average. Color: Yellow-Green Group 144A. Strength: Strong.
- *Peduncle.*—Length: About 15 mm. Diameter: About 4 mm. Color: Yellow-Green Group 145A. Texture: Smooth.

Flower bud development: Flower buds are borne single and in clusters of about 5 flower buds per stem. The inflorescence type resembles an umbel.

Flower bloom:

- *Fragrance.*—None.
- *Duration.*—The blooms have a duration on the plant of approximately 21 days. Petals fall cleanly away from plant after flowers have fully matured.
- *Size.*—Flower diameter is about 60 mm when open. Flower depth is 35 mm. The inflorescence is about 15 cm wide and 12 cm in height.
- *Flower shape.*—Rosette, very double, with many overlapping petals packed into quarter sections.
- *Shape of flower, side view.*—The upper portion is convex. The lower portion is concave.

Petalage: Under normal conditions, flowers have about 137 petals.

General tonality of flower: Open flowers are Red Group 43C. After about 10 days, Red Group 52C.

Petal color:

- *Upon opening, outer and inner petals.*—Upper surface: Red Group 43C. Lower surface: Red Group 52A.
- *Basal petal spots, upon opening.*—Upper surface: White Group 155A, small in size. Lower surface: White Group 155A, small in size.
- *After opening, outer and inner petals.*—Upper surface: Red Group 43C. Lower surface: Red Group 52B with shades of White Group 155A radiating from the basal petal spot.
- *Basal petal spots, after* opening.—Upper surface: White Group 155A, small in size. Lower surface: White Group 155A, small in size.

Petals:

- *Petal reflex.*—Very strong.
- *Margin.*—Entire and uniform. Moderate undulations.
- *Shape.*—Broad and elliptic. Apex shape: Rounded. Base shape: Acute.
- *Size.*—30 mm (l) x 27 mm (w).
- *Texture.*—Smooth on upper and lower surface.
- *Thickness.*—Average.

Petaloids:

- *Size.*—10 mm (l) by 6 mm (w).
- *Quantity.*—About 50.
- *Shape.*—Elliptical with an acute base and rounded apices. Some petaloids are indistinguishable from reproductive flower parts.
- *Color.*—Red Group 43C upper and Red Group 52A lower surface, with basal intonations of White Group 155A.

Reproductive flower parts:

- *Pollen.*—Moderate amount, Yellow Group 4D in color.
- *Anthers.*—Size: 1.5 mm in length. Color: Green-White Group 157A. Quantity: 15 on average.
- *Filaments.*—Color: Green-White Group 157A. Length: 4 mm.
- *Pistils.*—Length: 6 mm. Quantity: 35 on average.
- *Stigmas.*—Color: Greyed-Yellow Group 160D.
- *Styles.*—Color: Green-White Group 157A.
- *Location of stigmas.*—Superior in location relative to the length of the filaments and the height of the anthers.
- *Hips.*—Ovate, Yellow-Green Group 146C, 16 mm in length by 9 mm wide.

Plant

Plant growth: Upright. Plants are 30 cm in height, and 30 cm wide.

Stems:

*Color of juvenile growth*.—Yellow-Green Group 144B.

*Color of mature growth*.—Yellow-Green Group 144A.

*Length*.—Canes are about 21 cm from the base of the plant to the flowering portion.

*Diameter*.—About 4 mm.

*Internodes*.—On mature canes about 35 to 40 mm between nodes.

*Surface texture*.—Young wood: Smooth. Older wood: Somewhat rough with small prickles.

Long prickles:

*Incidence*.—9 prickles per 10 cm of stem.

*Size*.—Average length of prickles on mature stems is 7 mm.

*Shape*.—Upper portion is linear. Lower portion is concave.

*Color*.—Juvenile prickles: Greyed-Yellow Group 160B. Mature prickles: Greyed-Yellow Group 160B.

Plant foliage:

*Compound leaf*.—97 mm (1) x 65 mm (w).

*Quantity*.—3 leaves per 10 cm of stem on average.

*Leaf bearing angle to the stem*.—45 to 60 degrees.

*Color of juvenile foliage*.—Upper side: Yellow-Green Group 146B with intonations of Greyed-Purple Group 183A at margins. Lower side: Yellow-Green Group 146C shaded with Greyed-Purple Group 183C.

*Color of mature foliage*.—Upper side: Yellow-Green Group 147A. Lower side: Yellow-Green Group 147B.

Plant leaves and leaflets:

*Stipules*.—Size: 11 mm long, 3 mm wide. Quantity: 2 per compound leaf. Shape: Linear, slightly broad based with outward extending apices. Margins: Finely serrated. Color: Yellow-Green Group 144A.

*Petiole*:.—Length: About 15 mm. Diameter: 2 mm. Upper surface color: Yellow-Green Group 144A. Lower surface color: Yellow-Green Group 144A.

*Rachis*.—Length: 37 mm on average. Upper surface color: Yellow-Green Group 144A. Lower surface color: Yellow-Green Group 144A.

*Leaflet*.—Quantity: Normally 7 leaflets. Margins: Serrated. Very light undulations. Size: Terminal leaflets are about 41 mm long, 28 mm wide. Shape: Generally broad elliptical. Base: Rounded. Apex: Mucronate. Texture: Smooth on the upper surface. Lower surface is somewhat rugose. Thickness: Average. Arrangement: Odd pinnate. Venation: Reticulate. Glossiness: The upper surface has a medium amount of leaf gloss. The lower surface is not glossy.

Disease resistance: Above average resistance to powdery mildew *Sphaerotheca pannosa* var. *rosae,* downy mildew *Peronospora sparsa,* rust *Phragmidium* spp., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpal106' substantially as described and illustrated herein.

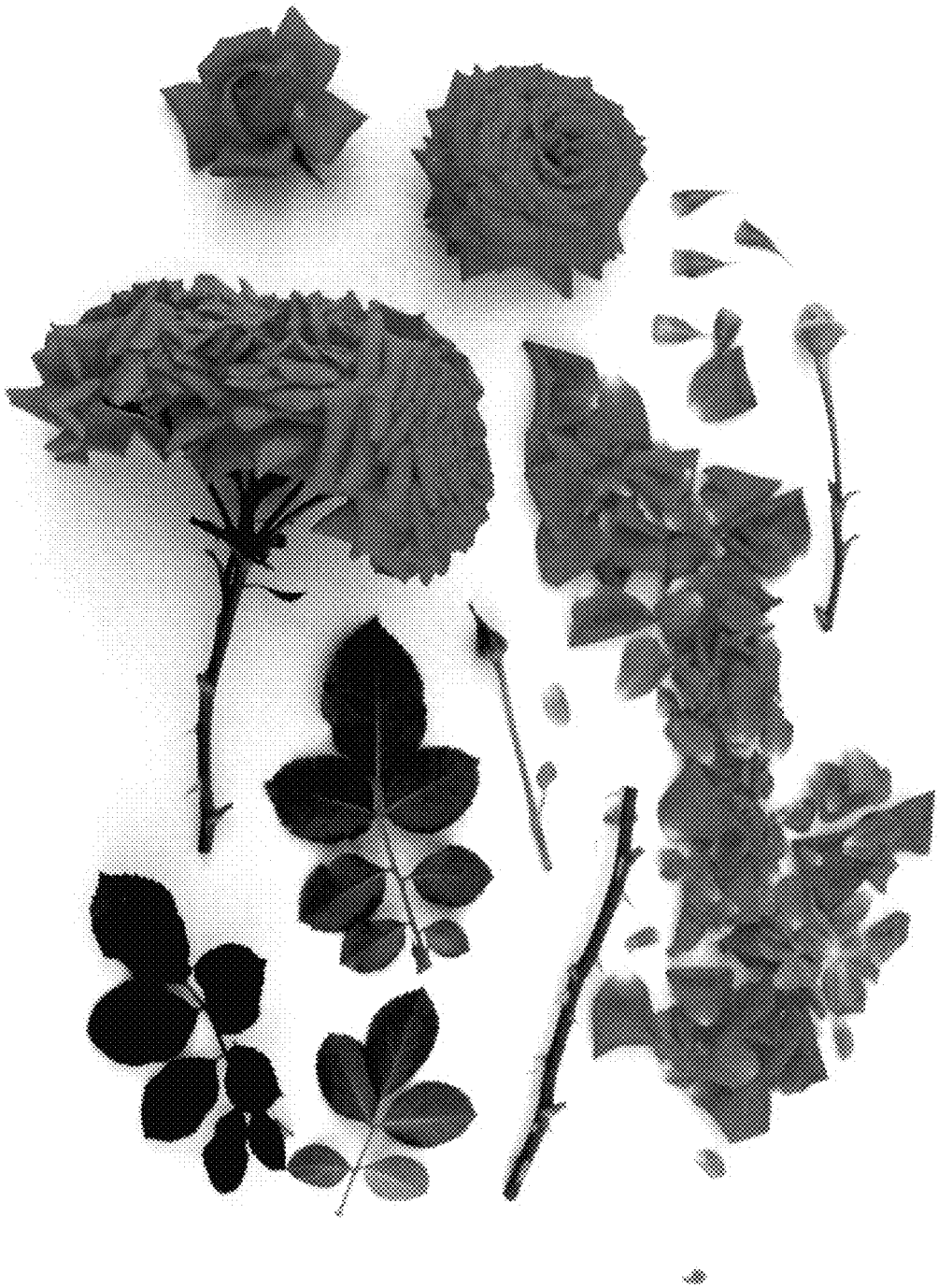

* * * * *